United States Patent [19]
Decker et al.

[11] Patent Number: 6,150,113
[45] Date of Patent: *Nov. 21, 2000

[54] METHOD FOR INCREASING SPECIFICITY IN COMPETITIVE IMMUNOASSAYS

[75] Inventors: Richard H. Decker, Deerfield; John A. Weare, Gurnee, both of Ill.

[73] Assignee: Abbott Laboratories, Abbott Park, Ill.

[ * ] Notice: This patent is subject to a terminal disclaimer.

[21] Appl. No.: 08/762,037

[22] Filed: Dec. 9, 1996

Related U.S. Application Data

[63] Continuation of application No. 08/357,369, Dec. 15, 1994, Pat. No. 5,681,695, which is a continuation of application No. 08/170,660, Dec. 20, 1993, abandoned, which is a continuation of application No. 07/592,015, Oct. 2, 1990, abandoned, which is a continuation of application No. 07/193,307, May 11, 1988, abandoned.

[51] Int. Cl.$^7$ .......................... G01N 33/53; G01N 33/576
[52] U.S. Cl. .............................. 435/7.1; 435/5; 435/7.92; 435/7.94
[58] Field of Search .............................. 435/5, 7.1, 7.36, 435/7.92, 7.94

[56] References Cited

U.S. PATENT DOCUMENTS

| | | |
|---|---|---|
| 4,234,564 | 11/1980 | McAleer et al. . |
| 4,683,136 | 7/1987 | Milich et al. . |

FOREIGN PATENT DOCUMENTS

| | | |
|---|---|---|
| 0012699 | 6/1980 | European Pat. Off. . |
| 0163312 | 12/1985 | European Pat. Off. . |
| 2383446 | 10/1980 | France . |
| 2016687 | 9/1979 | United Kingdom . |
| 2052059 | 1/1981 | United Kingdom . |
| 8703690 | 6/1987 | WIPO . |

OTHER PUBLICATIONS

Sherertz, et al., "Antibody to Hepatitis B surface antigen may not always indicate immunity to hepatitis B virus infection", *The New England Journal of Medicine*, 309(24): 1519 (1983).

Abbott Laboratories, Product Insert, "CORZYME®: Enzyme immunoassay for the detection of antibody to hepatitis B core antigen in serum or plasma" (1987).

Abbott Laboratories, Product Insert, "CORAB®: Radioimmunoassay for the detection of antibody to hepatitis B core antigen in serum or plasma" (1987).

Angarano, et al., *Biol. Abstracts* 72: Abstract No. 32079 (1981).

Cambiaso et al., "Particle counting immunoassay (PACIA). III. Automated determination of circulating immune complexes by inhibition of an agglutinating factor of mouse serum", *Journal of Immunological Methods*, 28:13–23 (1979).

Caspari, et al., "Unsatisfactory specificities and sensitivities of six enzyme immunoassays for antibodies to hepatitis B core antigen", *J. Clin. Micro*, 27/9:2067–2072 (1989).

Davis, et al., "'Immunology' an introduction to molecular and cellular principles of the immune responses", Second Ed., Copyright 1974, Harper Row, p. 410.

Deyo, et al., *Biol. Abstracts*, 70: Abstract No. 64854 (1980).

Howard, et al., "Core antigen and circulating anti–core antibody I hepatitis B infection", *Journal of Immunological Methods*, 14:291 (1977).

Kessler, et al., "Antibodies to hepatitis B surface antigen as the sole hepatitis B marker in hospital personnel", *Annals of Internal Medicine*, 103:21–26 (1985).

Prahl, "The C–terminal sequences of the heavy chains of human immunoglobulin G myeloma proteins of differing isotypes and allotypes", *Biochem. J.*, 105:1019–1028 (1967).

Robertson, et al., "Characterization of a reduction–sensitive factor from human plasma responsible for apparent false activity in competitive assays for antibody to hepatitis B core antigen", *J. Clin. Micro.*, 29/3:605–610 (1991).

Sallberg, et al., "Enzyme immunoassay for anti–hepatitis B core (HBc) immunoglobulin G1 and Significance of low–level results in competitive assays for anti–HBc", *Journal of Clinical Microbiology* 27/5: 849–853.

Shiraishi, et al., *Biol. Abstracts*, 80: Abstract No. 23240 (1985).

Slobin, et al., "The specific cleavage of immunoglobulin polypetide chains at cysteinyl residues", *The Journal of Biological Chemistry*, 243/8:1777–1786 (1968).

Spronk, et al., "Improvements in detection of antibody to hepatitis B core antigen by treating specimens with reducing agent in an automated microparticle enzyme immunoassay", *J. Clin. Micro.* , 29/3:611–616 (1991).

Weare, et al., "Improvement in the specificity of assays for detection of antibody to hepatitis B core antigen", *J. Clin. Micro.*, 29/3:600–604 (1991).

Weeks, et al., *Clin. Chem.*. 29/8: 1474–1479 (1983).

Yolken, et al., "Analysis of nonspecific reactions in enzyme–linked immunosorbent assay testing for human rotavirus", *J. Clin. Micro.*, 10/6:703–707 (1979).

*Primary Examiner*—Laurie Scheiner
*Attorney, Agent, or Firm*—Dianne Casuto; Priscilla E. Porembski

[57] ABSTRACT

The invention is an improved immunoassay and method for detection of antibody to hepatitis B core antigen (anti-HBc). The improved assay comprises the addition of a reducing agent to decrease the number of false positive reactions in the assay.

9 Claims, 12 Drawing Sheets

FIG. 15 □ A280 + CONTROL % INHIBITION ◇ CONTROL + CYSTEINE % INHIBITION

METHOD FOR INCREASING SPECIFICITY IN COMPETITIVE IMMUNOASSAYS

This is a CONTINUATION of U.S. patent application Ser. No. 08/357,369, filed Dec. 15, 1994, now U.S. Pat. No. 5,681,695, which is a CONTINUATION of U.S. patent application Ser. No. 08/170,660, filed Dec. 20, 1993 (abandoned), which is a CONTINUATION of U.S. patent application Ser. No. 07/592,015, filed Oct. 2, 1990 (abandoned), which is a CONTINUATION of U.S. patent application Ser. No. 07/193,307 filed May 11, 1988 (abandoned).

BACKGROUND OF THE INVENTION

Hepatitis B core antigen (HBcAg) is a particle from the core of the hepatitis B virion (HBV), sometimes referred to as the Dane particle. HBcAg is a potent immunogen which typically elicits a strong immune response persisting for years after HBV infection has cleared and is found in serum of patients with chronic HBV infections.

The detection of antibody to hepatitis B core antigen (anti-HBc) is used to monitor the progress of HBV infections. Anti-HBc is found in serum shortly after the appearance of hepatitis B surface antigen (HBsAg) and, in acute hepatitis B, will persist after the disappearance of HBsAg and before the appearance of detectable antibody to HBsAg (anti-HBs). Therefore, in the absence of HBsAg and anti-HBs, anti-HBc may be the only serological marker of recent hepatitis B infection and potentially infectious blood.

About ten years ago, a large study of transfusion-related viral infections revealed that donors who were positive for anti-HBc were often implicated in the transmission of other infectious agents to recipients. Vyas and Perkins, *New England J Med.*, 306: 749–750, 1981. Most notable was the finding that approximately 40% of the recipients of donor blood who subsequently developed non-A, non-B hepatitis infections (NANB) had received at least one unit of anti-HBc positive blood. While the scientific relationship of this association of NANB and anti-HBc has not been established, many scientists believe that it is an epidemiological association and that donors who have been exposed to hepatitis B are among those most likely to have been exposed as well to NANB. Because of the failure to date to identify a specific marker for NANB and because of the significant frequency of NANB in blood recipients, blood banks have turned to surrogate testing to improve the safety of the blood supply in the U.S. Detection of anti-HBc has been selected as one such surrogate test for lowering the transmission of NANB.

Immunoassays for the detection of anti-HBc are well known. Examples of such assays include the CORAB® radioimmunoassay and the CORZYME® enzyme immunoassay, both commercially available from Abbott Laboratories, North Chicago, Ill. These assays are competitive immunoassays in which anti-HBc in a biological sample competes with a constant amount of anti-HBc which is labeled with a detectable label for a limited number of binding sites on a solid phase coated with HBcAg. The proportion of bound labeled anti-HBc is inversely proportional to the concentration of anti-HBc in the biological sample.

The anti-HBc assays described above can be performed by one- or two-step methods. In the one-step procedure, a sample and labeled anti-HBc are mixed together and allowed to compete for HBcAg attached to a solid phase. In the two-step procedure the HBcAg on the solid phase is first reacted with the test sample and then with labeled anti-HBc in a second step. In either method, the amount of labeled anti-HBc bound to the solid phase is measured, and a reduction in the amount of labeled antibody is indicative of an antibody positive sample which is able to block binding of the labeled antibody.

False positives represent a problem in screening donor blood for anti-HBc because there are a large number of specimens which are positive only for anti-HBc with no other hepatitis marker present and no history or symptoms of disease. There is no simple way to confirm that these specimens are true positives. This is particularly troublesome when anti-HBc testing is used as a surrogate screening for NANB because the epidemiologic connection between the marker and the disease is not strong (85% of recipients of anti-HBc positive blood do not develop a known infection). Therefore, it is important to discriminate between anti-HBc positive specimens that relate to NANB and those which do not or are false positives.

SUMMARY OF THE INVENTION

We have discovered an improvement to immunoassays and methods of detection for anti-HBc such as those described above which prevent the detection of anti-HBc positive reactions which are by several criteria false positives. The improvement comprises the addition of a reducing agent such as sulfhydryl compounds including 2-mercaptoethanol (2ME), dithiothreitol (DTT), dithioerythritol (DTE), cysteine or other reducing agents such as bisulfite solutions especially a metabisulfite solution (MBS) or sodium bisulfite.

The reducing agent can be introduced into the immunoassay in several ways. The sample may be treated with the chemical prior to the start of the assay. In a one-step assay, the sample, labelled reagent, solid phase and the reducing agent may be added simultaneously or in one of the diluents for the sample, labelled reagent or solid phase. However, if the labelled reagent contains a reducing agent-sensitive component such as an enzyme, for example, horseradish peroxidase, the reducing agent should not come in contact with the enzyme and is introduced in a separate step in a two-step assay. In such a two-step assay, the sample and solid phase are incubated together before the addition of the labelled reagent in a second step. The reducing agent may be added in either the first or second step but is preferably added to the sample prior to addition of the solid phase or simultaneously with the sample and solid phase, and is most effective when added in the first incubation.

Surprisingly, the addition of a reducing agent to an assay for anti-HBc eliminates false positive specimens, especially those near the cut-off value, while having no significant effect on control values or true positive specimens. This results in a reduced number of samples that are reactive for anti-HBc only, i.e., with no other HBV markers or history of disease. This increased specificity for anti-HBc testing further increases specificity for blood bank surrogate testing for NANB, reducing the number of discarded blood units and saving donors from follow-up clinical evaluation to determine their own health status and future rejection as blood donors.

Although the interfering reactivity or factor which is being destroyed is not completely understood, it is a macromolecule with physical characteristics different from IgG. The interfering activity may be caused by a heterogenous factor, i.e., more than one molecule or a complex. The molecular weight of the interfering factor is greater than 500,000, it is extremely unstable in the presence of a reducing agent and is unstable below a pH of 4.5. This interfering factor is believed to be hydrophobic on the basis of its interaction with hydrophobic gels and is soluble in 30% $(NH_4)_2SO_4$ and precipitates at 50%. It is partially retained on CM or DEAE-cellulose. It is not believed that the interfering factor eliminated by the reducing agent is IgM, since it is unlikely that there would be a significant number of low level IgM-anti-HBc positive samples, and many samples containing the interfering factor failed to react in an IgM-capture assay such as Corzyme M (available from Abbott Laboratories, North Chicago, Ill.). Further, the biochemical evidence is that the interfering factor is differentially destroyed by MBS or cysteine and is unstable in the presence of other reducing agents to a different degree than IgM. For example, at the concentrations of reducing agents and under the conditions employed in the invention, IgM would not be completely destroyed, whereas, the interfering factor is totally eliminated. Also, although the interfering factor coelutes with IgM on Sephacryl S-300, the nonspecific activity is lost upon chromatography on Sepharose 6B while low levels of IgM-specific activity are recovered in the expected fractions. It is noteworthy that the inactivation of the interfering factor on Sepharose 6B in the absence of reducing agent. It appears therefore that not only reducing agents, but also gel filtration, causes disruption of a possible complex or aggregate which is responsible for the interfering activity.

DETAILED DESCRIPTION OF THE INVENTION

Two populations of specimens were used to demonstrate the invention. The first population (I) is a group of selected anti-HBc positive sera which were defined as true positives because they possessed other markers of hepatitis B or were from subjects with a previous history of hepatitis B and whose reactivity was associated with gamma globulins. The second population (II) is a group of serum specimens from donors without other markers of hepatitis B or a history of hepatitis B and whose reactivity could not be clearly associated with gamma globulins. Most of the group II specimens were weak positives when they were tested in a one-step anti-HBc assay, but usually exhibited stronger anti-HBc-like reactivity when tested with a two-step procedure. Group I positives were generally strongly reactive in both test procedures; randomly selected sera of this group were diluted so that they simulated the level of activity of group II positives in the study. Both groups I and II were tested by conditions described in detail below, with and without reducing agents.

EXAMPLE 1

0.1 ml samples in groups I and II were placed in duplicate reaction wells, along with negative and positive controls, and 10 ul of 0.3% 2-mercaptoethanol (2-ME) in $H_2O$ was added to one each of the duplicates, while 10 ul $H_2O$ was added to the other. 0.1 ml of $^{125}$I-labeled anti-HBc was added to all wells, followed by an HBcAg-coated ¼ inch polystyrene bead to all wells. Trays were gently shaken and allowed to incubate overnight at room temperature. All beads were washed 3 times with distilled water and transferred to test tubes for counting for 1 minute in a gamma scintillation counter. The positivity or negativity of each was calculated, as was the degree (%) inhibition from negative control for each specimen both with and without reducing reagent according to the formula:

$$\frac{\text{cpm Neg. Control} - \text{cpm Sample}}{\text{cpm Neg. Control} - \text{cpm Pos. Control}} \times 100$$

(cpm = counts per minute)

By this calculation, a sample giving a value equal to or greater than 50% is judged as positive in the test. The effect of the addition of the reducing reagents to the specimens was evaluated by several criteria:

a) Comparing negative and positive control values, with and without reducing agent;

b) Making a side-by-side comparison of % inhibition values of each specimen in group I and group II, with or without reducing reagents;

c) Plotting the frequency of the % inhibition values for each group with and without reducing reagent, and comparing the distribution of specimen values within each group, with or without reducing agents.

Figure 1:
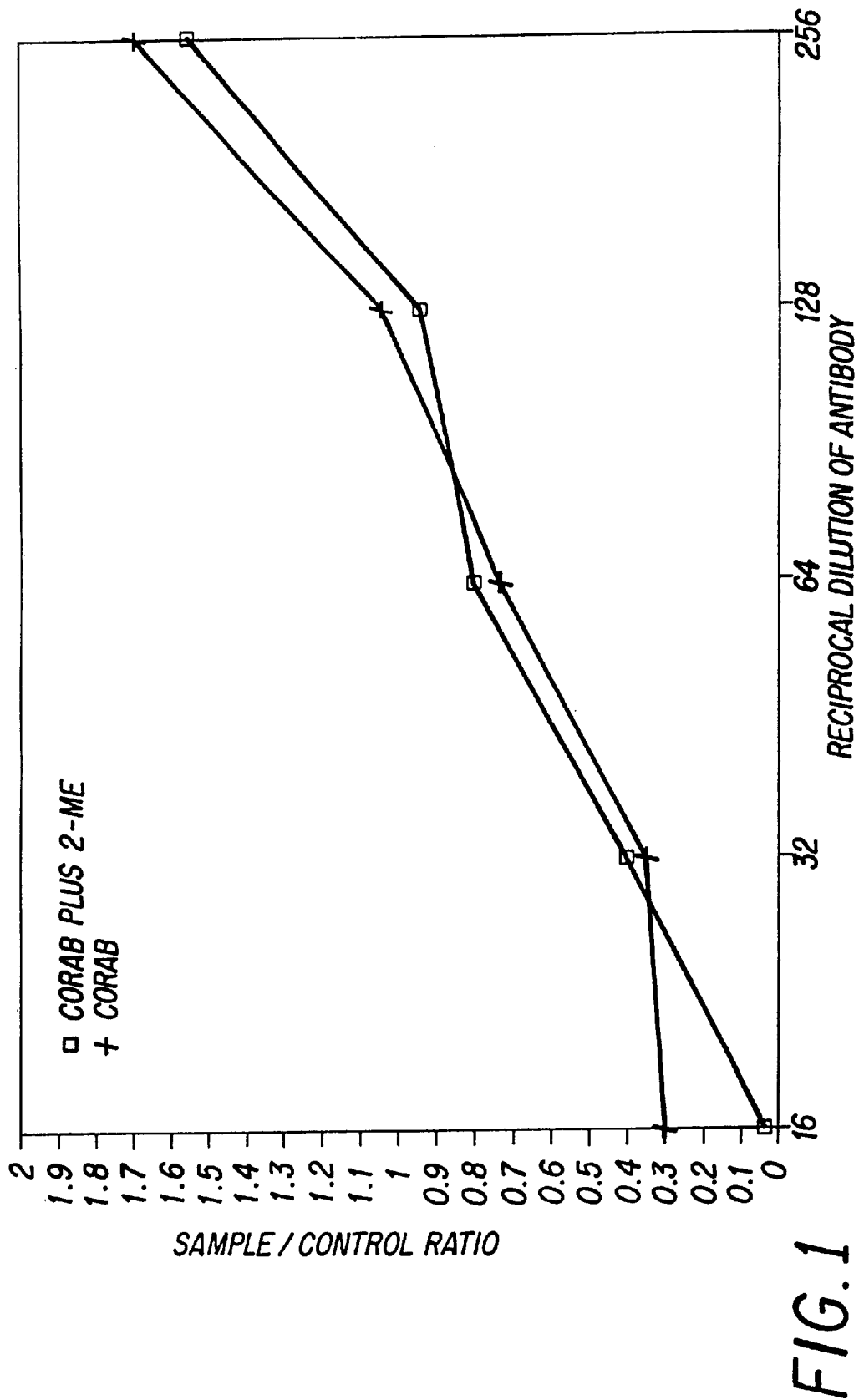
FIG. 1 is a graph showing a serial dilution of a true positive anti-HBc sample tested for anti-HBc with and without reducing agent.
Figure 2:
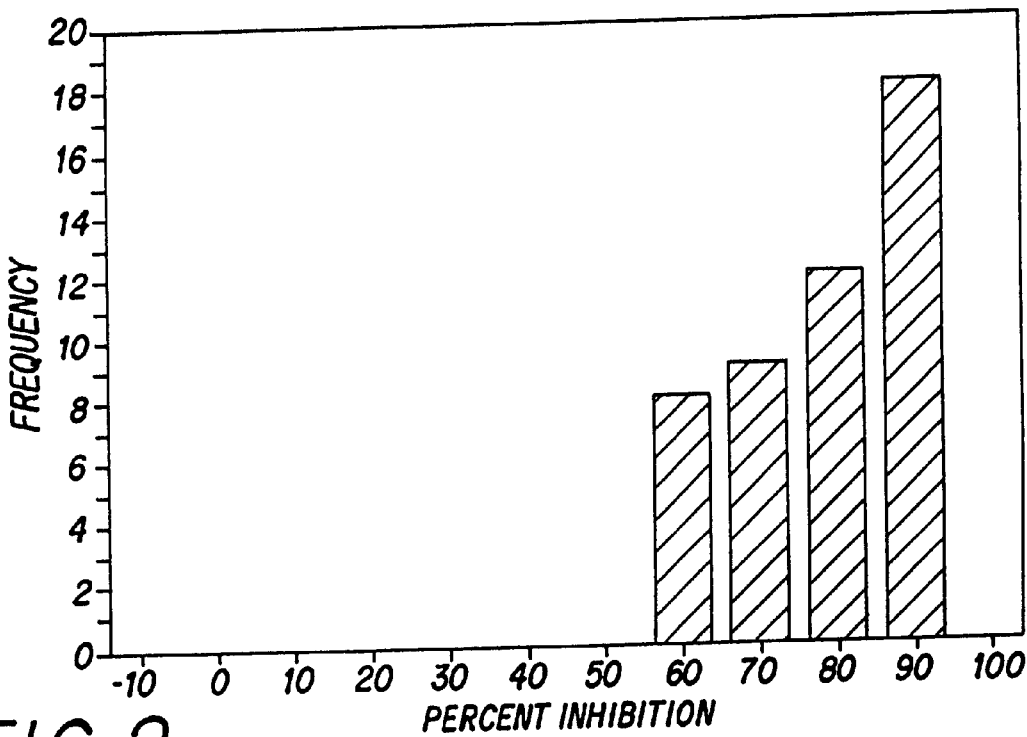
FIGS. 2 and 3 are bar graphs showing Group I anti-HBc samples tested for anti-HBc with and without reducing agent.
Figure 3:
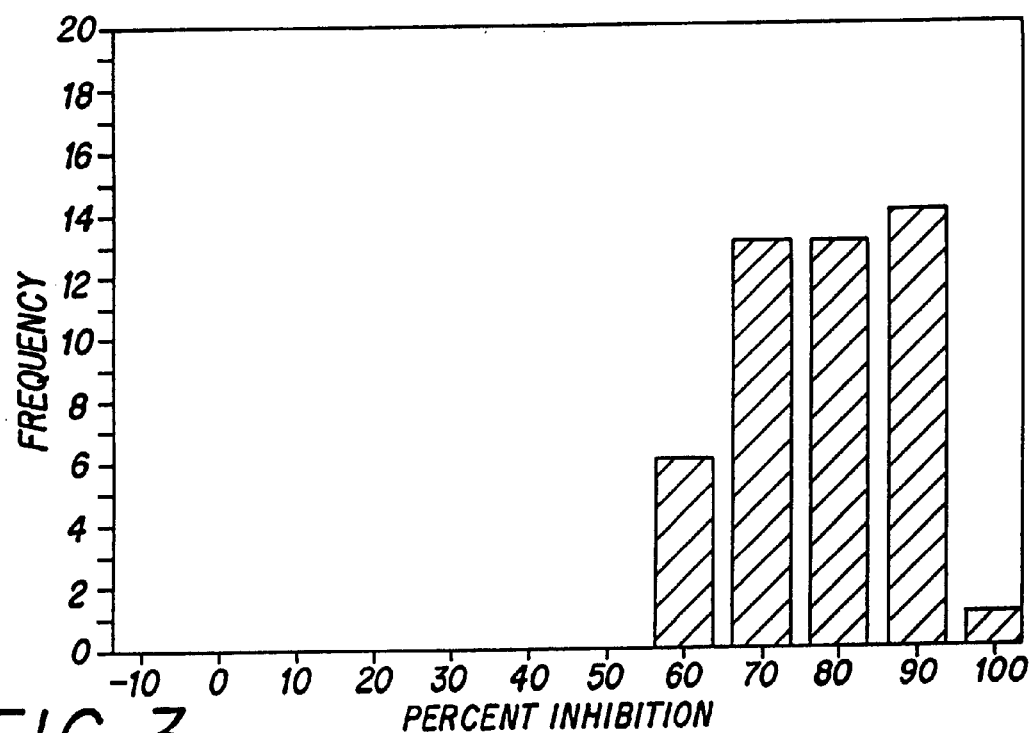
Figure 4:
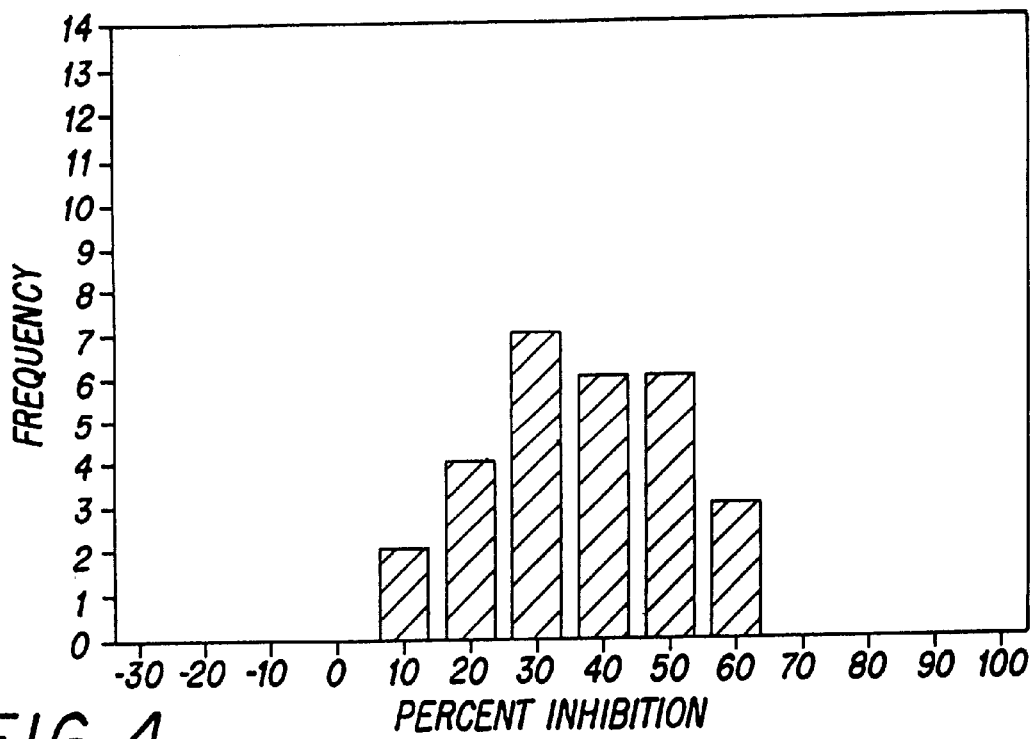
FIGS. 4 and 5 are bar graphs showing Group II false positive samples tested for anti-HBc with and without reducing agent.
Figure 5:
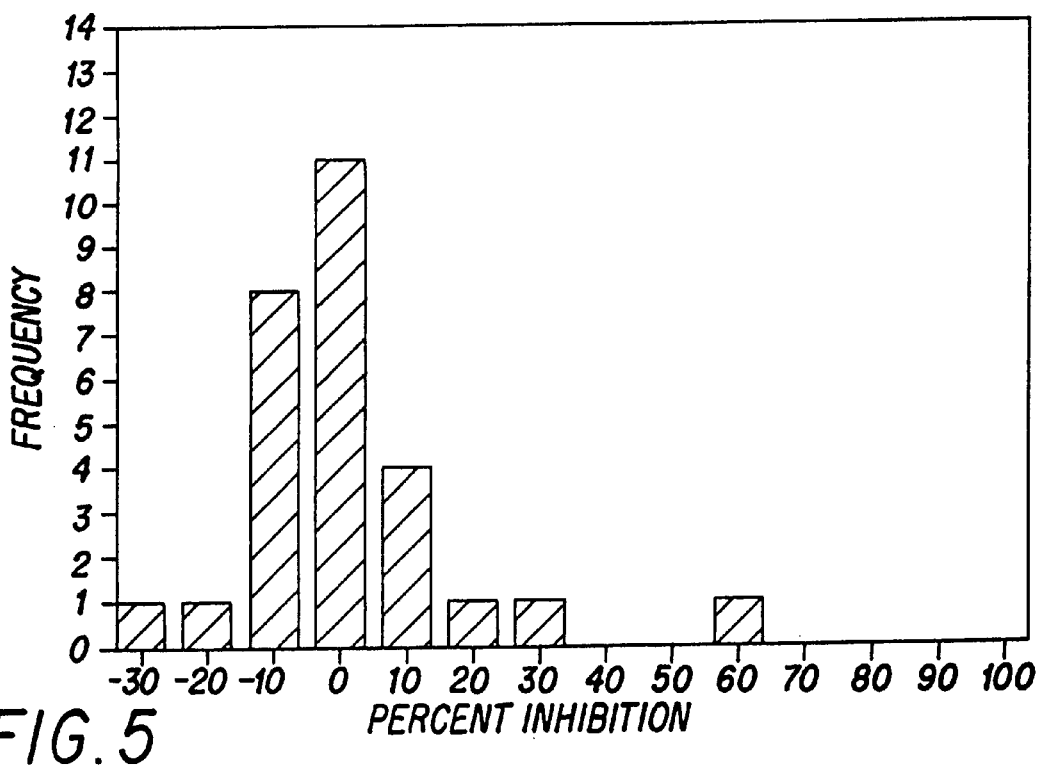

Results in FIGS. 1–3 show that sensitivity and detectability of the test for true positives (group I) were unaffected by the addition of reducing agents. Table I shows that the absolute values for negative and positive controls were also not affected significantly by another reducing agent (MBS). On the other hand, most specimens of the group II class were clearly affected, as shown in FIGS. 4 and 5, such that each specimen lost most of its ability to inhibit labeled antibody, and behaved like a negative specimen.

EXAMPLE 2

0.1 ml of specimens in groups I and II were placed in duplicate in reaction wells, as in Example 1, but 0.1 ml of saline solution was added to each, followed by 10 ul of 0.5% $NaHSO_3$ in $H_2O$ to one of the duplicates, and 10 ul $H_2O$ to the other duplicate. (0.2% $Na_2S_2O_5$ in $H_2O$ can be substituted for the 0.5% $NaHSO_3$.) An HBcAg-coated bead was added to each well, and the trays were gently shaken and incubated overnight at room temperature. After washing the beads, they were incubated with 0.2 ml of anti-HBc IgG conjugated with horseradish peroxidase (HRP) for 1 hour at 40°. Beads were again washed 3 times with distilled water and transferred to clean reaction tubes. Bead-bound antibody-HRP was detected by adding a solution of o-phenylenediamine (OPD) in citrate-phosphate buffer containing 0.02% hydrogen peroxide, to each bead for 30 minutes, stopping the reaction with $H_2SO_4$ and reading the degree of absorbance at A492. A significant reduction in color intensity was an indication of reactivity from a true or false antibody positive specimen, and positivity was calculated according to the following formula:

$$0.4 \times NCV + 0.6 \times PCV = \text{Cutoff Value}$$

(NCV=Neg. Control Mean Value; PCV=Pos. Control Mean Value) Specimens with absorbance values equal to or lower than the Cutoff Value were considered positive and specimens with values greater than the Cutoff Value were considered negative. Additionally, the degree (%) inhibition from negative control for each specimen, both with and without reducing reagent was calculated according to the formula of Example 1, but substituting A492 values for CPM, and the effect of the addition of reducing reagent to specimens was also evaluated according to the criteria described in Example 1.

Figure 6:
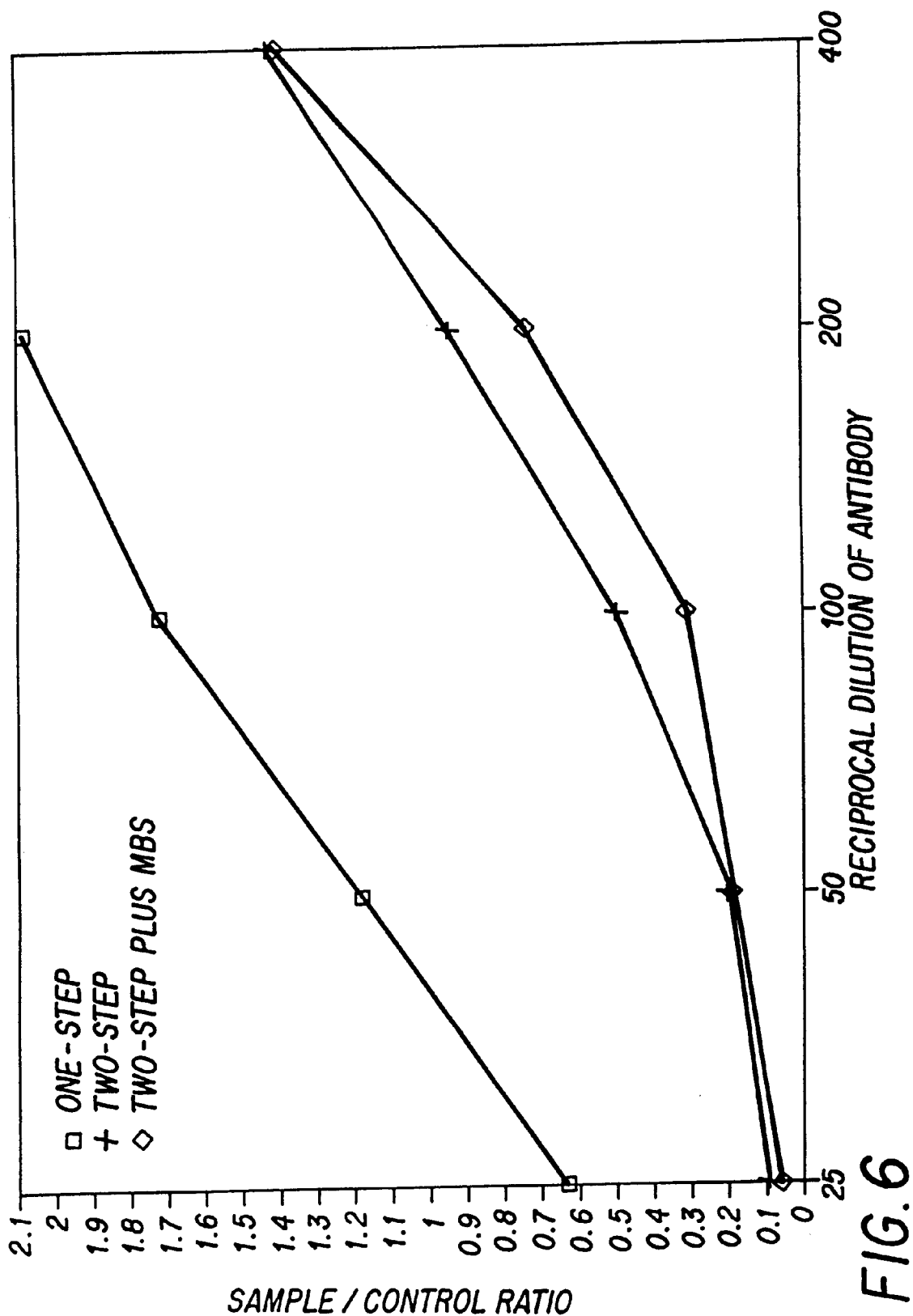
FIG. 6 is a graph demonstrating serial dilution testing of a true positive anti-HBc sample with and without reducing agent.
Figure 7:
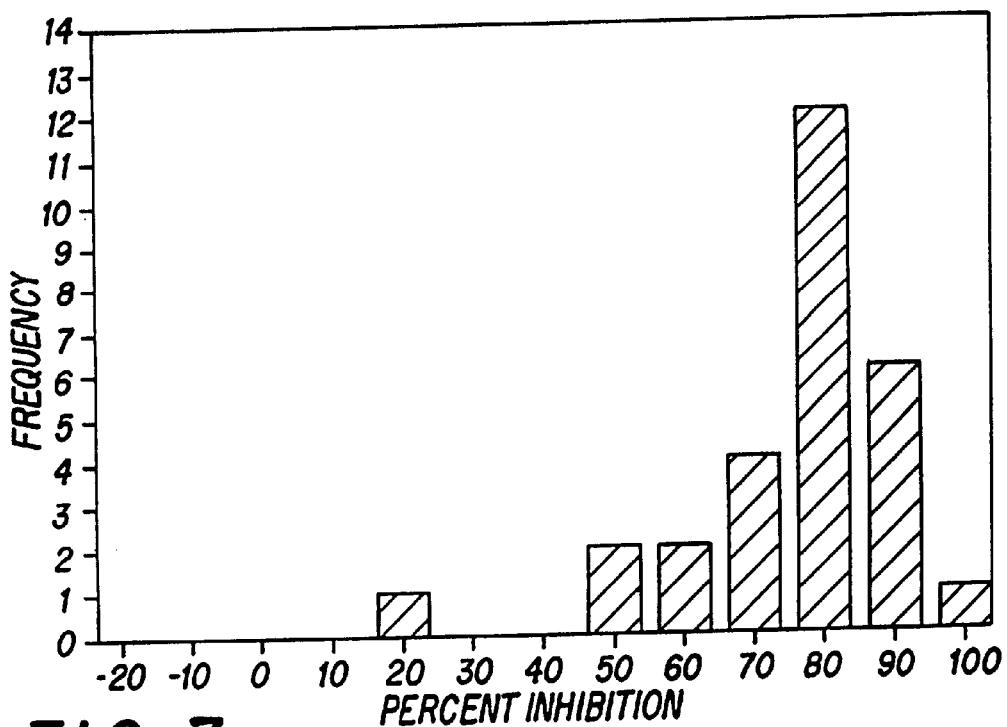
FIGS. 7 and 8 are bar graphs showing Group II false positive samples tested for anti-HBc in the presence and absence of reducing agent.
Figure 8:
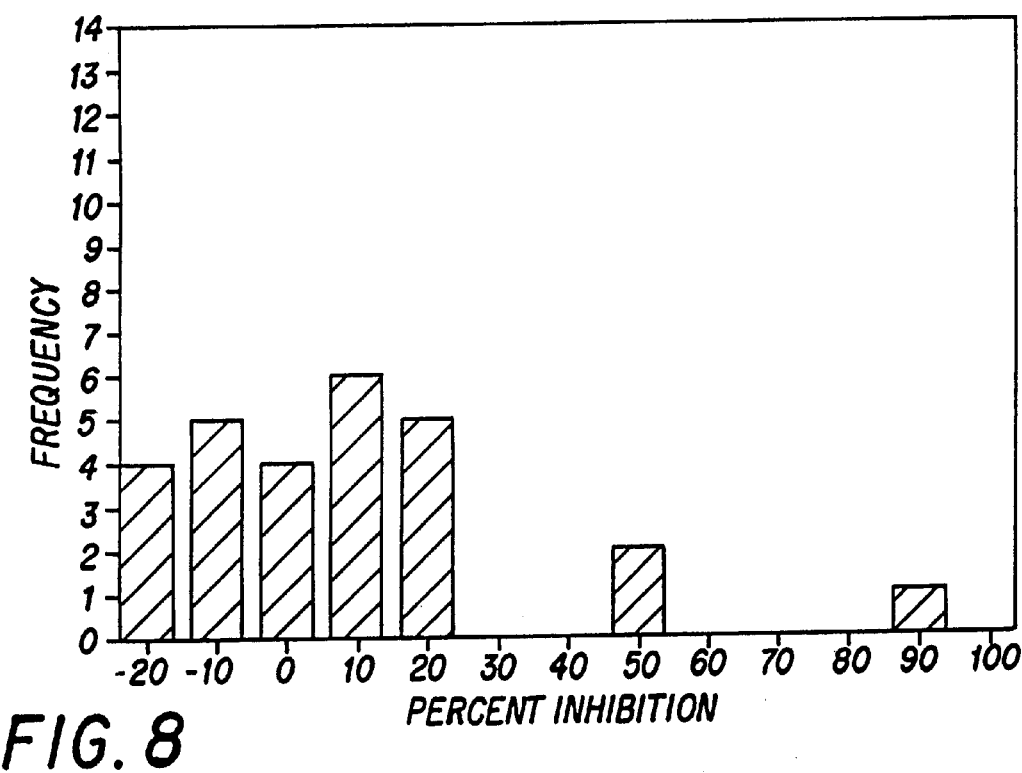
Figure 9:
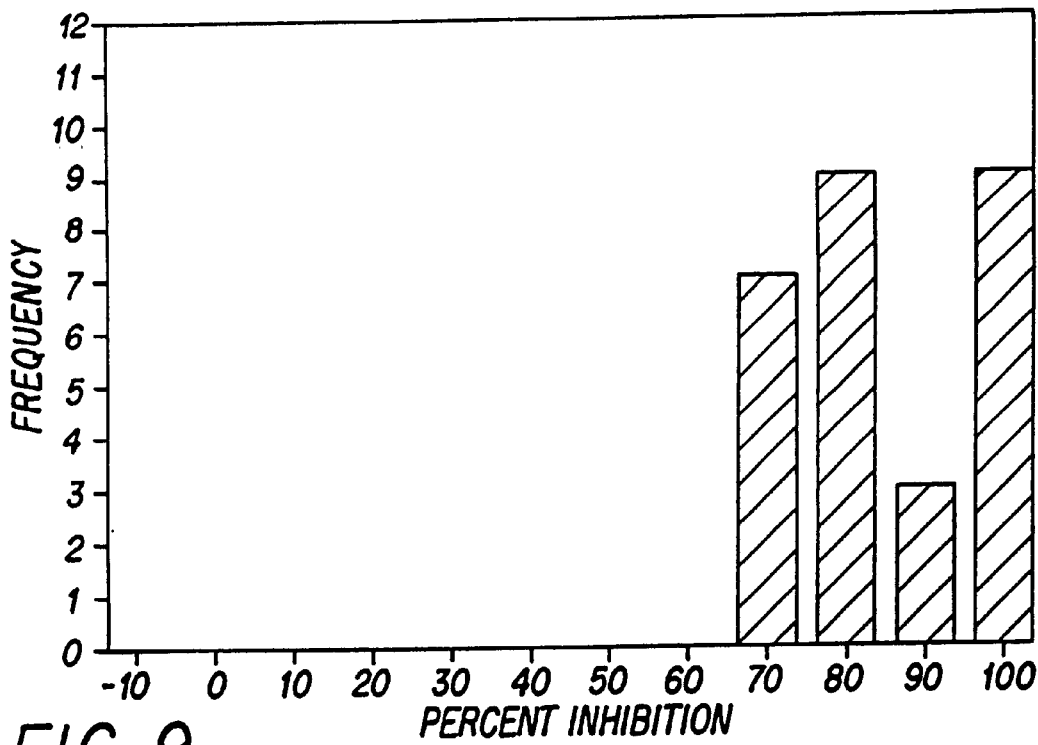
FIGS. 9 and 10 are histograms of Group I positive samples tested for anti-HBc in the presence and absence of reducing agent.
Figure 10:
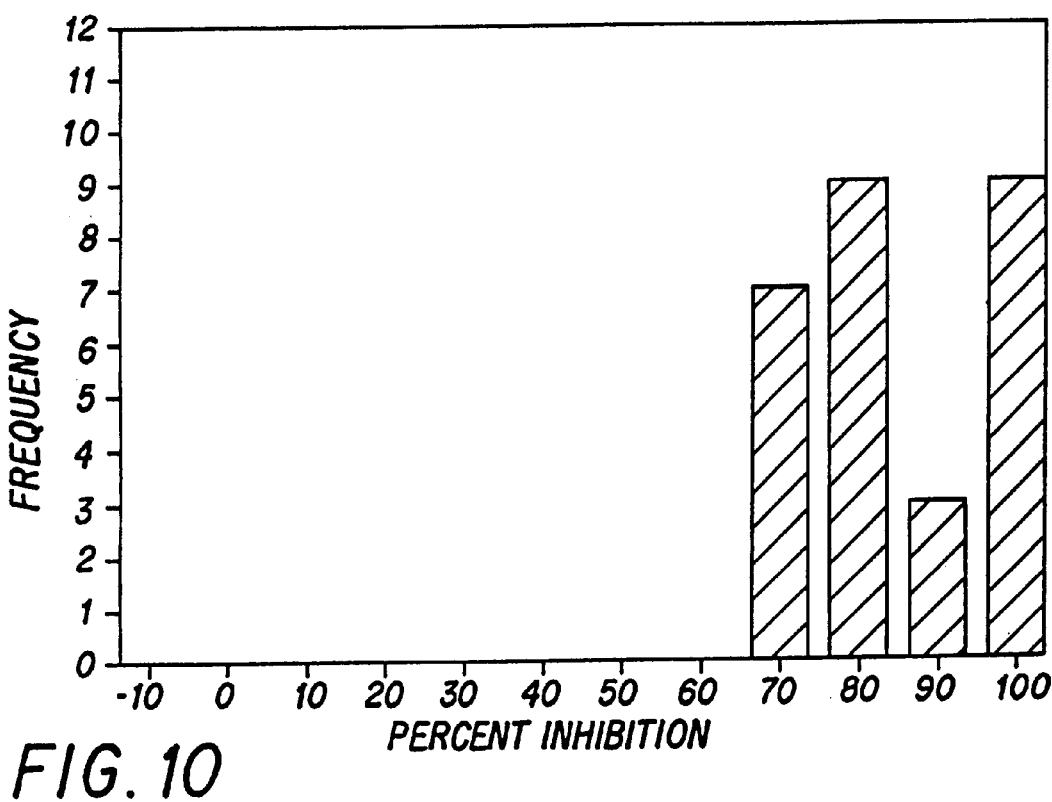

Results are shown in FIGS. 6–10, which show similar findings to Example 1, namely that the reducing agents had little or no effect on sensitivity of the test, FIG. 6, and that reducing agents selectively affect group II positives but not group I positives (FIGS. 7–10). The calculated values of neutralization for each specimen were found to be greater in the two-step enzyme immunoassay than in the one-step radioimmunoassay, because the two-step is several dilutions more sensitive than the one-step procedure.

EXAMPLE 3

A microparticle chemiluminescence immunoassay for anti-HBc was performed as follows:

A. Preparation of HBcAg-Coated Microparticles

Recombinant DNA hepatitis B core antigen (rHBcAg) was coupled to carboxylated polystyrene latex microparticles (Seragen Diagnostics, Indianapolis, Ind., 0.188 um) using a two-step procedure. First, purified polyclonal human anti-HBc at 2.7 ug/mg latex particles in the presence of normal human serum (1.0 ul/mg) was coupled using 1-ethyl-3-(3-dimethylaminopropyl) carbodiimide (EDAC, 43 ug/mg) in 0.015 M MES buffer (2-[N-morpholino] ethanesulfonic acid), pH 4.8, for 2 hours at room temperature. Bangs, "Uniform Latex Particles", Seragen Diagnostics, 1984. The antibody undercoated particles were then washed three times in 0.1 M Tris buffer, pH 7.2, containing 0.9% NaCl, 0.03% EDTA and 0.05% Tween-20 by centrifugation (40,000×g for 20 minutes) and resuspended in 0.1 M Tris buffer, pH 7.2, containing 0.9% NaCl, 0.03% EDTA and 0.03% bovine serum albumin. rHBcAg (0.2 ug/mg) was then immunologically adsorbed on the undercoated particles by slow rotation overnight at room temperature. Particles were washed three times as before and dispersed through a 25 gauge needle and stored in 0.01 M sodium phosphate, pH 7.2, containing 0.15 M NaCl, 0.1% bovine serum albumin, 0.01% Tween-20 and 0.1% sodium azide (Microparticle Diluent). Percent solids was determined by light scattering at 500 nanometers. Coated particles were stored concentrated (typically 5–10% solids) and diluted in storage buffer to a working concentration (0.036%) before each assay. In an alternative method, rHBcAg was coupled directly to the microparticles by the EDAC method. The anti-HBc undercoating method is preferred.

B. Preparation of Acridinium-Labeled Anti-HBc

Acridinium-labeled purified anti-HBc (human) was prepared using an EDAC coupling procedure on the active ester. Briefly, 1 mg of B-alanine acridinium was dissolved in 100 ul anhydrous DMF and activated by sequential addition of 50 ul N-hydroxylsuccinimide (NHS) (5.75 mg/ml) and 50 ul EDAC (19.2 mg/ml) (molar ratio NHS:EDAC=1:2). The reaction proceeded in the dark at room temperature for 30 minutes. Protein A purified human anti-HBc was dialyzed (3×) against PBS, 0.5% CHAPS, pH 6.3, overnight at 2–8° C. Activated acridinium was added to dialyzed antibody (30:1 molar excess) and the reaction mixture stirred for 30 minutes at room temperature. After dialysis versus the same buffer, the preparation was centrifuged and the supernatant chromatographed on a Beckman TSK 250 HPLC column equilibrated with the same buffer. Individual fractions (1 ml) were analyzed by UV spectroscopy at 369 and 280 nm to determine incorporation of acridinium (typically 3:1). Conjugate was stored in concentrated fractions (approximately 100 ug/ml) at 2–8° C. and diluted in 0.01 M sodium phosphate containing 14.8 g/L EDTA, 0.1% sodium azide, 0.4% Tween-20, 50% (V:V) normal calf serum and 2% (V:V) normal human serum, pH 6.3, before each assay (Conjugate Diluent).

C. Preparation of Stable Aqueous Cysteine Reagent

In water, cysteine oxidizes to cystine which is relatively insoluble and forms a white precipitate. The oxidation is enhanced by the presence of metal ions notably copper, iron and by a neutral or slightly alkaline pH. A procedure for preparing relatively stable solutions of cysteine is described below.

Distilled water was deionized using a Barnstead Water-I Deionizer to a final resistance of 18 megaohms. Cysteine (Sigma Chemical Co., Free Base), EDTA and DTT were added to final concentrations of 200, 10 and 1 mm respectively. The pH of the solution was between 4.5 and 5.0 and was not adjusted. Aliquots of the solution were stored in closed glass vials at room temperature and at 2–8° C.

Stability was assessed by the lack of cystine precipitate which formed in aqueous solutions without the chelating agent (EDTA) and reductant (DTT). After two weeks no precipitate was evident at either temperature (Table II). Stability was also assessed by the effectiveness of this reagent over time to eliminate non-specific anti-HBc activity from two plasma samples (S9 and S14), which were similar in anti-HBc activity to the Group II samples described above, as shown in Table II. Two week stability was sufficient for practical utilization of the reagent in the microparticle assay described below.

D. Microparticle Assay 100 ul duplicates of samples including a sensitivity panel sample (1.23 Paul Erhlich Units/ml, Panel 7), two samples, S9 and S14, which were similar in anti-HBc reactivity to Group II samples described above, and negative and positive controls were added to a microtiter plate. Next, 50 ul of the cysteine solution containing 200 mM cysteine, 10 mM ethylenediaminetetraacetic acid (EDTA) and 1 mM dithiothreitol (DTT), described above, was added in duplicate, and H₂O was added as a control also in duplicate. 50 ul of the HBcAg-coated microparticles (0.036% solids) were added to all wells. This reaction mixture was incubated for 20 minutes in a 40° water bath.

166 ul of each reaction mixture was transferred to a microparticle capture/flow-through glass fiber filter funnel (Abbott Laboratories, North Chicago, Ill.) which was prewetted with 50 ul of 0.1% Tween-20. Each capture membrane was then washed twice with 50 ul of 0.1% Tween-20. 20 ul of the acridinium-labeled anti-HBc (375 ng/ml) was added to the surface of each capture membrane and incubated at room temperature for 20 minutes. The capture membranes were then washed twice with 100 ul and once with 50 ul of 0.1% Tween-20.

The membranes were then transferred to a chemiluminescence reader where approximately 100 ul of a trigger solution comprising 0.3% H₂O₂ in 0.25 N NaOH was delivered to each membrane. The amount of light generated by the acridinium-labelled reagent bound to the microparticles was determined and is inversely proportional to the amount of anti-HBc present in the sample. Results are shown in Table III. Assay sensitivity as determined by percent inhibition (% I) of Panel 7 was slightly improved in the presence of the cysteine reagent. There was a 10–20% signal loss in the negative control in the presence of cysteine. The type of activity (interfering factor) found in Group II type samples, S9 and S14, was eliminated when the assay was performed in the presence of cysteine.

EXAMPLE 4

Plasma samples designated 52, 71, 166 and 277, Panel 7 and negative and positive controls were tested according to the microparticle assay procedure of Example 3, except that 10 ul of 0:75 M cysteine (Sigma, free base) prepared fresh was used instead of the cysteine solution containing EDTA and DTT. The samples were run both with and without cysteine.

As can be seen in Table IV, Sample 277 is a truly negative sample. Samples 71 and 166 are borderline positive samples which are similar in anti-HBc activity to Group II samples, except that these are unaffected by treatment with the reducing agent cysteine, indicating that these are indeed borderline or discrepant samples. Samples 52 and 189 are borderline samples which are also similar to Group II samples, but in the presence of the reducing reagent these samples proved to be negative. Each sample was also tested with and without 26.3 ul of a sensitivity panel sample (Panel 5) equivalent to 1.23 PEI U/ml to determine the effect of spiking these samples with a true positive anti-HBc sample with and without cysteine. Results are shown in Table IV. Panel 7 produced 71.8% and 80.7% inhibition in the absence and presence of cysteine, respectively. The negative control spiked with an amount of Panel 5 equivalent to panel 7 gave 73.7% and 80.8% inhibition in the absence and presence of cysteine, respectively. The average percent inhibition in unspiked plasma samples dropped from 31.8% to 21.0% with addition of cysteine. The average percent inhibition of plasma samples spiked with the equivalent of panel 7 was 67.1% and 71.5% in the absence and presence of cysteine, respectively.

EXAMPLE 5

Sensitivity panel samples which are known positive for anti-HBc (Panels 5, 6, 7, 8 and 9) were tested by the microparticle assay procedure of Example 3. Results are shown in Table V. There was no effect on assay sensitivity when the cysteine reagent was utilized.

EXAMPLE 6

Plasma samples designated 25, 31, 76, 91, 177 and 189 were tested with a commercially available anti-HBc kit (Corab®, Abbott Laboratories, North Chicago, Ill.) with and without addition of 10 ul of a reducing agent, 0.5 M sodium metabisulfite. Also, as in Example 4, samples were tested with and without addition of 26.3 ul of a positive anti-HBc sample (Panel 5). Results are shown in Table VI. As can be seen from the Table, Sample 25 is a truly negative sample. Samples 31 and 91 are discrepant samples which are confirmed as negative upon addition of the reducing agent. Sample 177 does not respond to treatment with MBS indicating that this sample is an elevated negative. As can be seen from Table VI, all anti-HBc positive samples, including Panel 7 and samples which were spiked with Panel 5 were not affected by the addition of MBS.

EXAMPLE 7

Figure 11A:
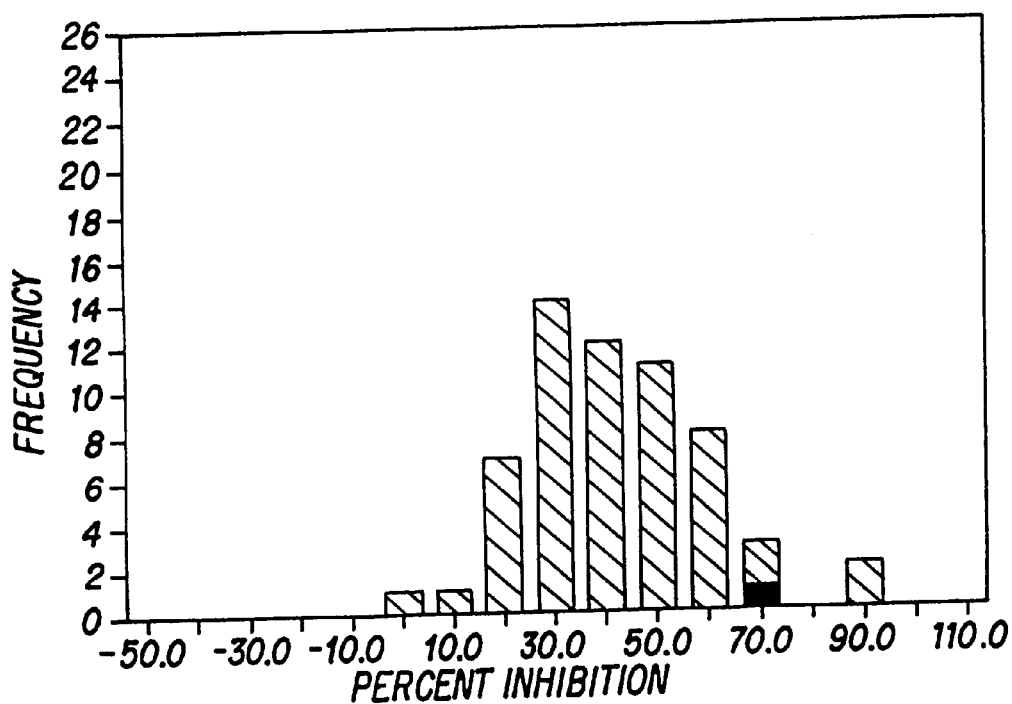
FIG. 11 shows anti-HBc borderline (Group II) samples tested for anti-HBc with and without MBS.
Figure 11B:
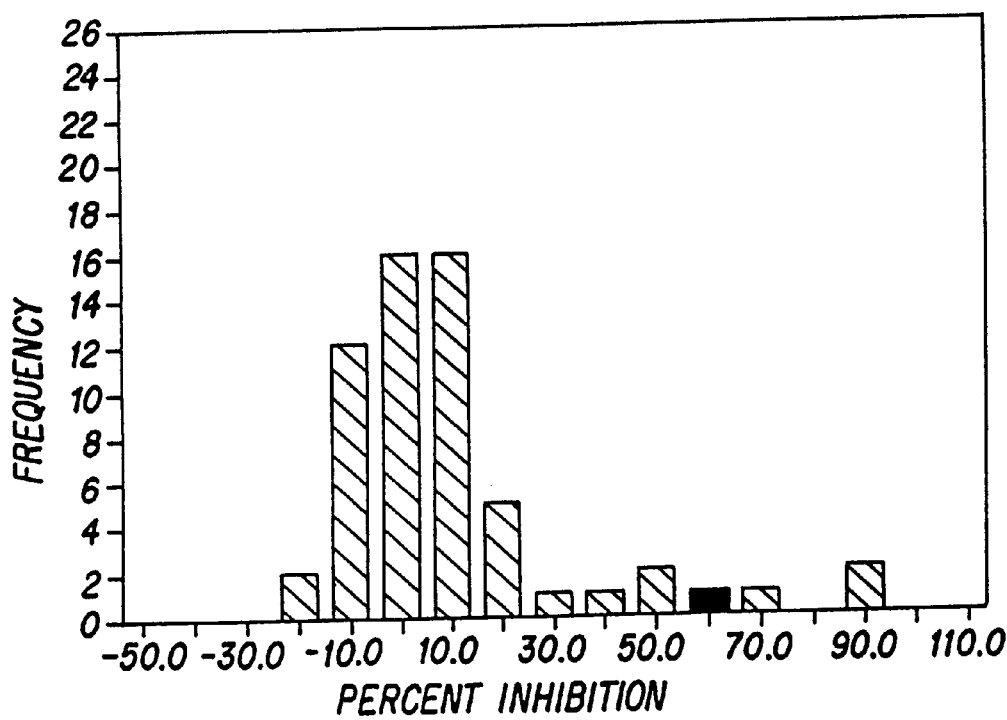

56 plasma samples with anti-HBc reactivity similar to Group II were tested by the method described in Example 6. These samples were identified as having discrepant results when tested by commercially available anti-HBc assays (Corzyme and Corab, Abbott Laboratories) and by the microparticle assay method described in Example 3, above, without reducing agents. Data are shown graphically in FIG. 11.

EXAMPLE 8

Figure 12A:
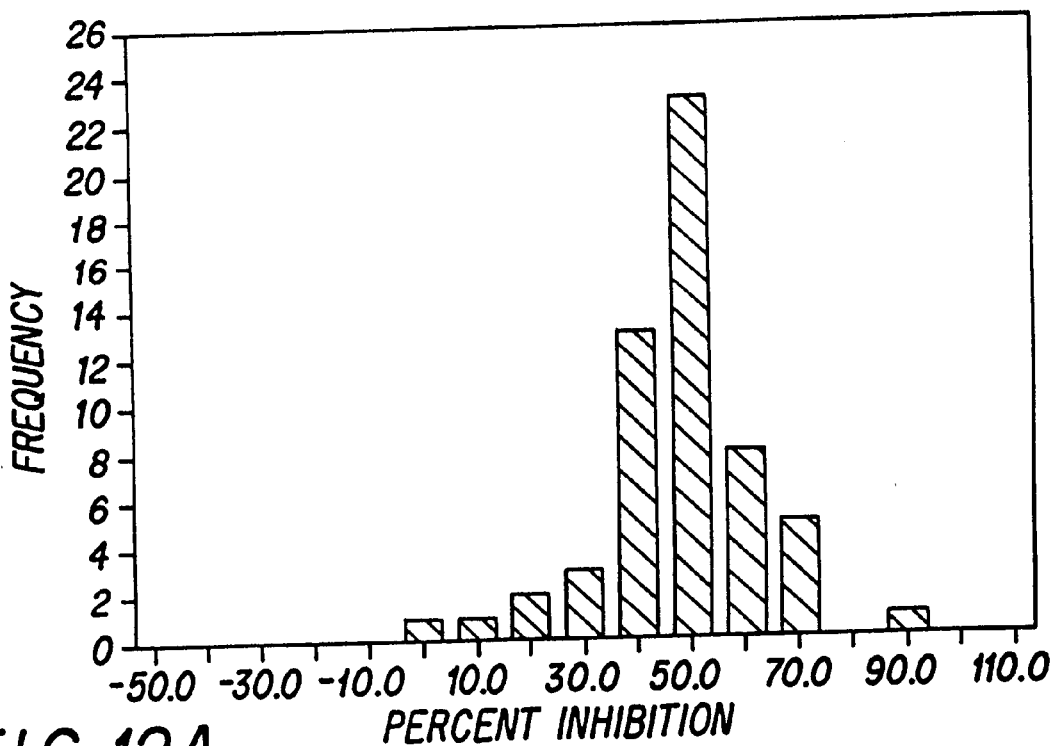
FIG. 12 demonstrates anti-HBc borderline (Group II) samples tested for anti-HBc with and without cysteine.
Figure 12B:
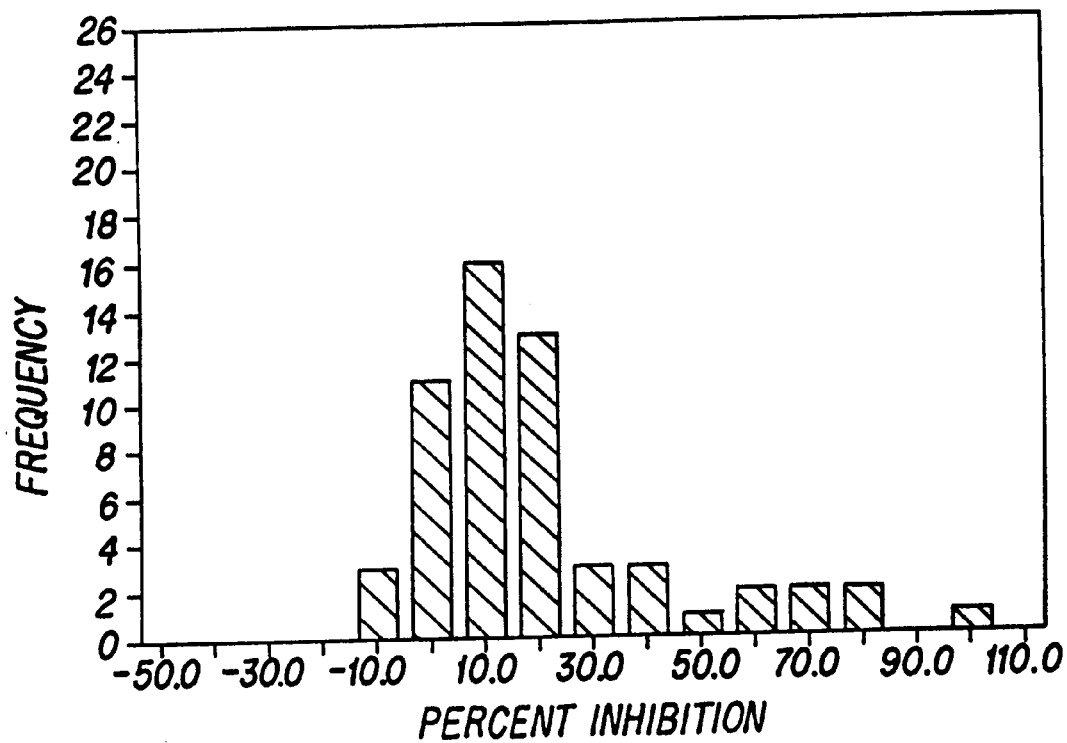
Figure 13:
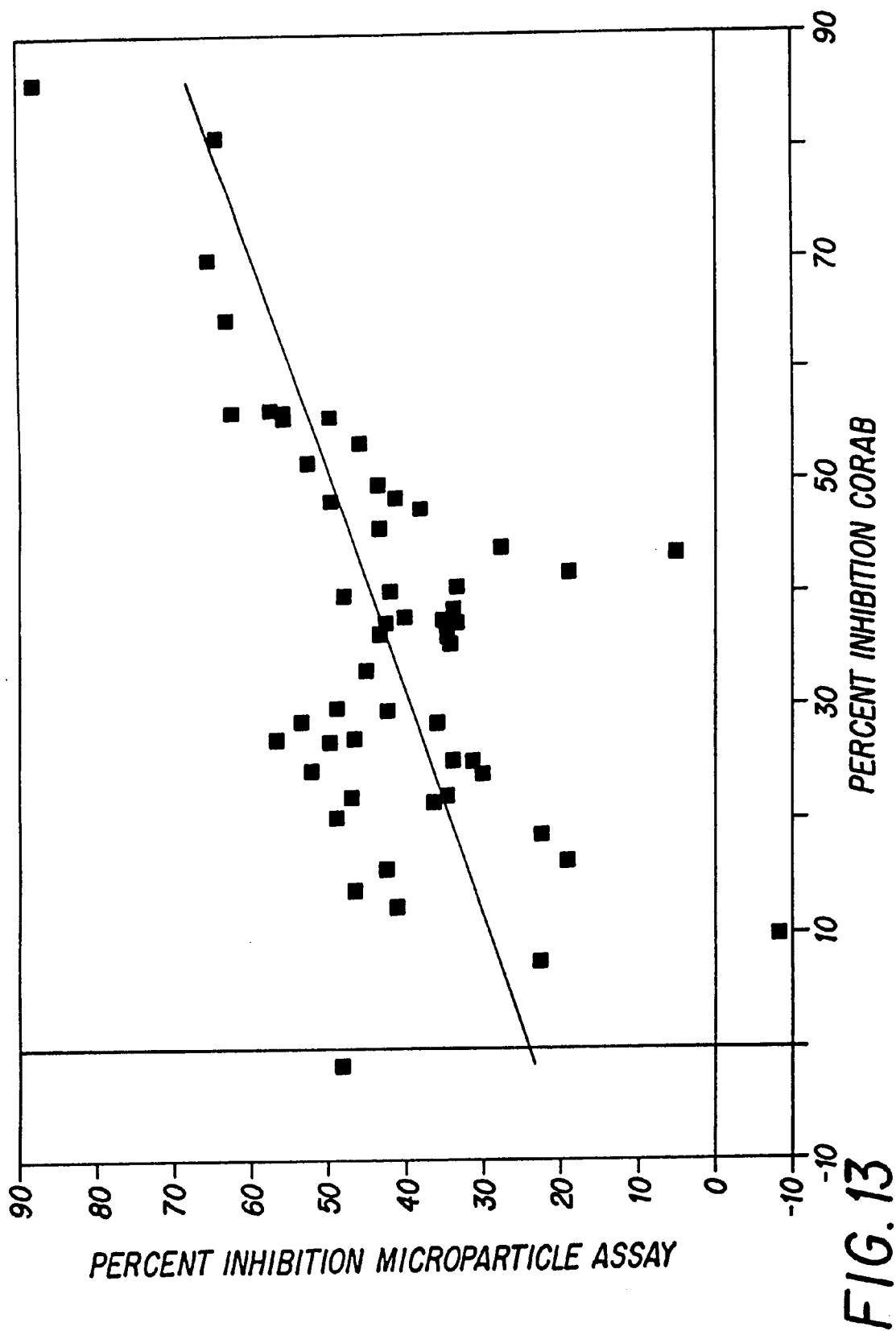
FIG. 13 is a graphic comparison of two assays for anti-HBc without reducing agent.
Figure 14:
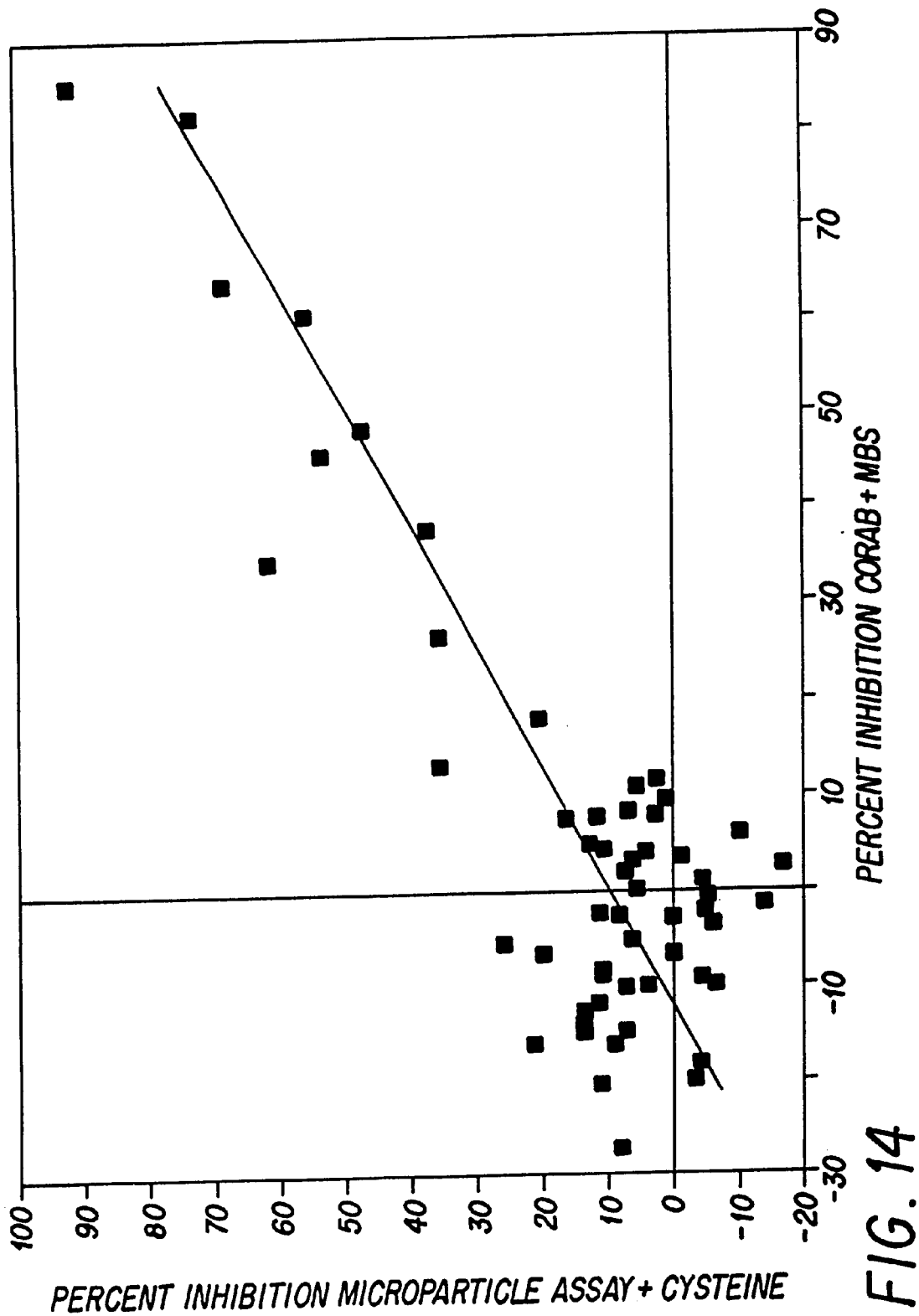
FIG. 14 is a graphic comparison of two assays for anti-HBc with reducing agent.

The plasma samples described in Example 7 were tested according to the microparticle assay procedure described in Example 3. Data are shown graphically in FIG. 12. The correlation between the data of Example 7 and this Example 8 in the absence of metabisulfite and cysteine, respectively, are shown in FIG. 13. The correlation between the data of Example 7 and this Example 8 in the presence of metabisulfite and cysteine, respectively, are shown in FIG. 14.

EXAMPLE 9

Figure 15:
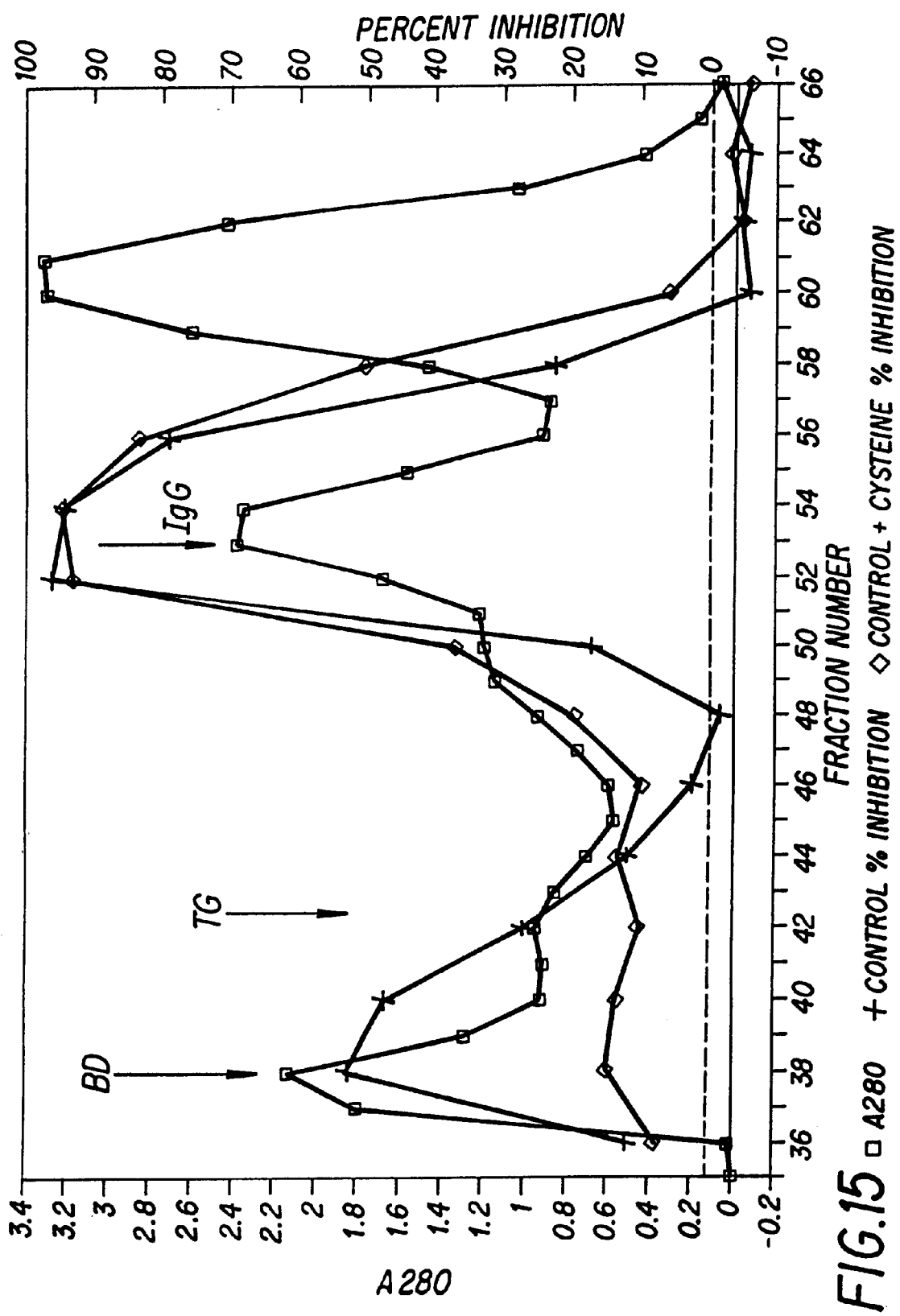
FIG. 15 is an absorbance and anti-HBc activity elution profile for a true positive anti-HBc sample.

The absorbance and anti-HBc activity of an anti-HBc positive sample (Sample 209) is shown in FIG. 15. This sample displayed 86.3% and 85.6% inhibition when tested in the Corab assay in the presence and absence of metabisulfite, respectively. Briefly, 2 ml of recalcified Sample 209 was applied to a Sephacryl S-300 column (2.5×50 cm) equilibrated with PBS. 2.5 ml fractions were collected at a flow rate of 20 ml/hr. Fractions were assayed using the microparticle assay of Example 3 except that an approximately 5 fold increase in sensitivity was implemented by using increasing incubation time and decreasing the amount of anti-HBc conjugate. As shown in FIG. 15, in the absence of reducing agent, two peaks of activity were detected. The first inhibitory peak was not detected when assayed in the presence of cysteine. The second and major inhibitory peak, which co-eluted with the IgG protein peak, was unaffected by cysteine treatment. The immunoglobulin G associated anti-HBc activity is specific for non-acute hepatitis B infection.

EXAMPLE 10

Figure 16:
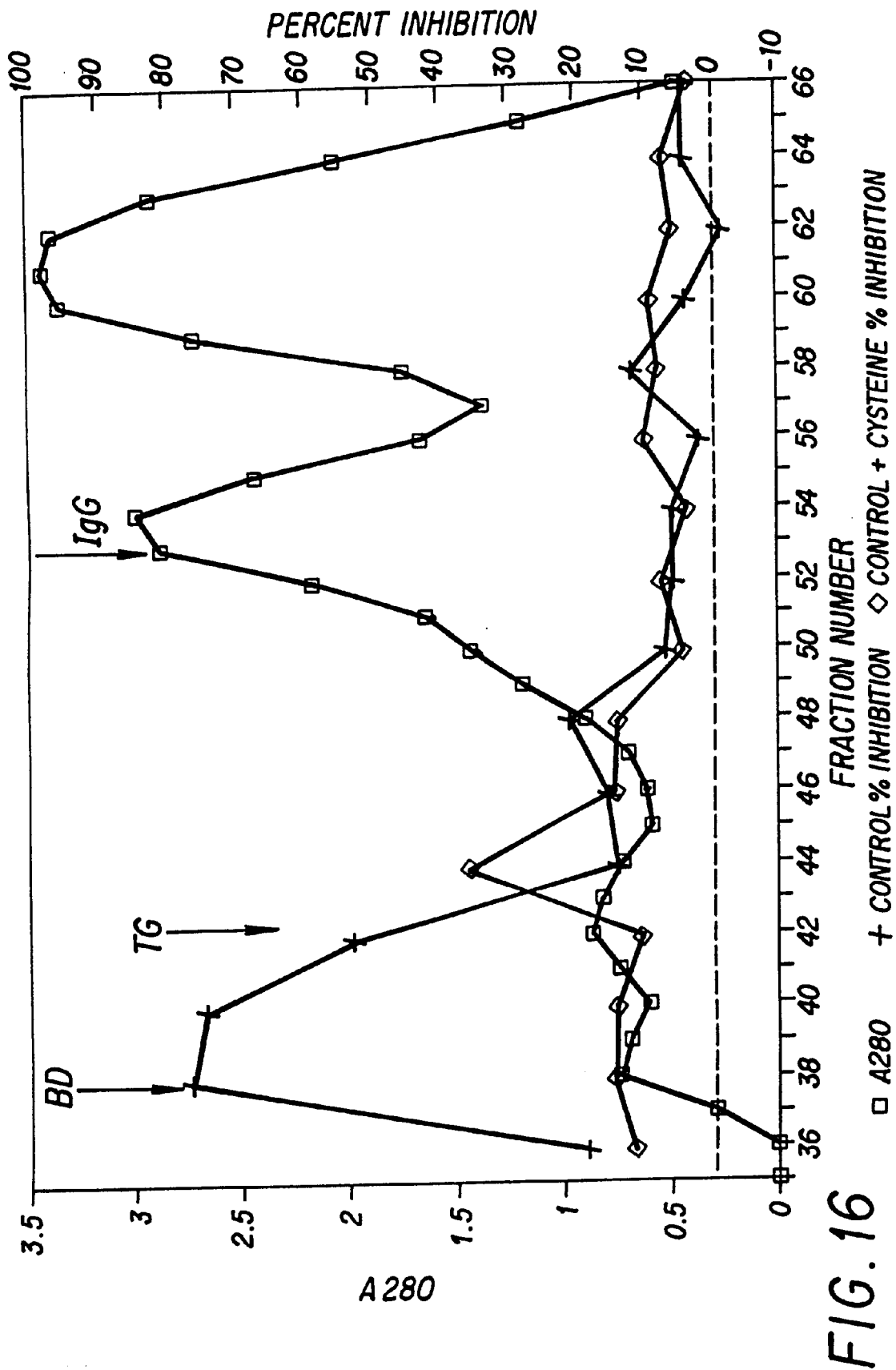
FIG. 16 is an absorbance and anti-HBc activity elution profile for a borderline (Group II) sample.

3 ml of a borderline positive sample (Sample 9) was tested according to the procedure of Example 9. The sample displayed 56.8% and 5.2% inhibition when assayed by the Corab assay in the absence and presence of metabisulfite, respectively. The absorbance and anti-HBc activity elution profile of Sample 9 is shown in FIG. 16. In the absence of reducing agent, a single inhibitory peak was seen near the void volume of the column. This peak was not detected when assayed in the presence of cysteine, and was clearly resolved form the IgG protein peak. This non-IgG reactivity is not believed to be a result of Hepatitis B infection and is therefore nonspecific.

The improved anti-HBc assay of the invention has many advantages. These include reduction in the number of borderline reactive anti-HBc-positive samples, including reduction in the number of samples which are positive for anti-HBc only with no other marker of hepatitis or disease history being present. By reducing the number of borderline or false positive samples in blood donor screening, the nation's blood supply will be enhanced and future donors will not be unnecessarily excluded.

While specific examples have been given to illustrate the invention, it is to be understood that those skilled in the art will recognize variations which come within the scope and spirit of the invention as claimed. For example, the improved assays can be performed in one or more steps using a variety of labelled reagents and instrumentation which are well known to those skilled in the art.

TABLE 1

Effect of Sodium Metabisulfite (MBS, 0.5%) on the inhibition values of 10 low positives from group I (true anti-HBc), tested by CORAB

| | Percent Inhibition in CORAB | |
|---|---|---|
| Specimen | no MBS | + MBS |
| 1 | 58 | 63 |
| 2 | 60 | 63 |
| 3 | 60 | 65 |
| 4 | 62 | 62 |
| 5 | 62 | 61 |
| 6 | 63 | 63 |
| 7 | 67 | 58 |
| 8 | 70 | 61 |
| 9 | 68 | 65 |
| 10 | 68 | 68 |
| Mean, NC (cpm) | 9782 | 9819 |
| Mean, PC (cpm) | 466 | 399 |

TABLE II

Stability of cysteine reagent at room temperature (RT) and at 2–8° C.

| | | Percent Inhibition | | | | | | | |
|---|---|---|---|---|---|---|---|---|---|
| | | Panel 7 | | | Sample S9 | | | Sample S14 | | |
| Day | PPT | control | RT | 2–8° C. | control | RT | 2–8° C. | control | RT | 2–8° C. |
| 0 | NO | 70.7 | | | 50.0 | | | 38.5 | | |
| 4 | NO | 69.6 | 71.5 | 74.0 | 45.7 | 45.7 | −12.6 | 28.9 | −27.3 | −0.6 |
| 7 | NO | 68.8 | 76.8 | 70.0 | 36.4 | 36.4 | 0.8 | 20.3 | −13.6 | −19.7 |
| 10 | NO | 62.8 | 69.9 | 73.6 | 28.9 | 28.9 | −13.5 | 14.8 | −14.8 | −17.2 |
| 14 | NO | 78.6 | 77.2 | 72.0 | 48.7 | 48.7 | −3.6 | 36.4 | −7.9 | −11.1 |
| 17 | NO | 65.1 | 63.1 | 67.1 | 45.8 | 45.8 | −2.9 | 35.0 | −10.1 | 0.0 |
| 21 | NO | 71.2 | 63.1 | 71.9 | 46.1 | 46.1 | −7.8 | 33.0 | −0.7 | −4.0 |

TABLE III

| | TEST SOLUTION | | | | | |
|---|---|---|---|---|---|---|
| | WATER (CONTROL) | | | 200 mM CYSTEINE | | |
| | (COUNTS) | % CV | % I | (COUNTS) | % CV | % I |
| Negative Control | 27265 | 5.7 | — | 23992 | 5.2 | — |
| Positive Control | 6255 | 1.6 | — | 5000 | 3.0 | — |
| Panel 7 | 12370 | 2.6 | 70.9 | 9511 | 1.5 | 76.3 |
| Plasma S9 | 16762 | 0.1 | 50.0 | 23377 | 0.7 | 3.2 |
| Plasma S14 | 19177 | 1.5 | 38.5 | 23421 | 1.8 | 3.0 |

% CV = PERCENT COEFFICIENT OF VARIATION

TABLE IV

| | RECOVERY EXPERIMENT | | | | | |
|---|---|---|---|---|---|---|
| | CONTROL | | | + CYSTEINE | | |
| | <cpm> | % CV | % I | <cpm> | % CV | % I |
| NC | 23811 | 1.7 | | 20856 | 2.1 | |
| PC | 4695 | 0.8 | | 4035 | 7.0 | |
| 7 | 10081 | 2.5 | 71.8 | 7528 | — | 80.7 |
| NC* OBI | 9733 | 12.1 | 73.7 | 7501 | 0.6 | 80.8 |
| 277 | 23944 | 6.8 | −0.7 | 22554 | 0.7 | −2.5 |
| 277* | 11106 | 7.0 | 66.5 | 9709 | 3.6 | 68.6 |
| 71 | 18858 | 2.5 | 25.9 | 15597 | 4.6 | 36.0 |
| 71* | 10563 | 1.7 | 69.3 | 9480 | 0.5 | 69.9 |
| 166 | 15646 | 1.1 | 42.7 | 12342 | 8.4 | 54.0 |
| 166* | 9971 | 1.4 | 72.4 | 7502 | 2.2 | 80.8 |
| 52 | 15610 | 1.4 | 42.9 | 20983 | 1.7 | 6.2 |
| 52* | 11948 | 0.2 | 62.1 | 9833 | 5.5 | 67.9 |
| 189 | 14598 | 2.1 | 48.2 | 20098 | 0.8 | 11.1 |
| 189* | 11393 | 4.7 | 65.0 | 9366 | 10.1 | 70.5 |
| X | | | 31.8 | | | 21.0 |
| X* | | | 67.1 | | | 71.5 |

*SPIKED WITH 26.3 ul PANEL 5 = 7 1.23 PEI u/ml (PANEL 7)

TABLE V

|  | CONTROL | | | + CYSTEINE | | |
| --- | --- | --- | --- | --- | --- | --- |
|  | mean counts | % CV | % I | mean counts | % CV | % I |
| Negative control | 29381 | 1.5 | — | 24494 | 3.8 | — |
| Positive control | 6832 | 5.1 | — | 5678 | 1.4 | — |
| Panel 5 | 9308 | 2.3 | 89.0 | 8177 | 2.3 | 86.7 |
| Panel 6 | 10116 | 2.9 | 85.4 | 8444 | 6.7 | 85.3 |
| Panel 7 | 11668 | 1.7 | 78.6 | 9972 | 5.2 | 77.2 |
| Panel 8 | 17191 | 0.9 | 54.1 | 14431 | 1.5 | 53.5 |
| Panel 9 | 22782 | 3.0 | 29.3 | 20548 | 2.1 | 21.0 |

TABLE VI

RECOVERY EXPERIMENT

|  | CORAB | | | CORAB + MBS | | |
| --- | --- | --- | --- | --- | --- | --- |
|  | <cpm> | % CV | % I | <cpm> | % CV | % I |
| NC | 19275 | 0.6 |  | 20856 | 2.5 |  |
| PC | 380 | 15.8 |  | 350 | 5.1 |  |
| PANEL 7 | 6413 | 6.7 | 68.1 | 6297 | 5.2 | 71.0 |
| NC* | 6213 | 9.4 | 69.1 | 5755 | 3.3 | 73.6 |
| OBI 25 | 19802 |  | -2.8 | 19301 |  | 7.6 |
| OBI 25* | 6433 |  | 68.0 | 5626 |  | 74.3 |
| OBI 31 | 12476 |  | 36.0 | 18733 |  | 10.4 |
| OBI 31* | 5786 |  | 71.4 | 5364 |  | 75.6 |
| OBI 91 | 10140 |  | 48.4 | 18651 |  | 10.8 |
| OBI 91* | 5068 |  | 75.2 | 5479 |  | 75.0 |
| OBI 76 | 16218 |  | 16.2 | 19667 |  | 5.8 |
| OBI 76* | 5952 |  | 70.5 | 5650 |  | 74.2 |
| OBI 177 | 15904 |  | 17.8 | 14395 |  | 31.5 |
| OBI 177* | 5895 |  | 70.8 | 5596 |  | 74.4 |
| OBI 189 | 13191 |  | 32.2 | 20350 |  | 2.5 |
| OBI 189* | 5777 |  | 71.4 | 5463 |  | 75.1 |
| <Sx> |  |  | 24.6 |  |  | 11.4 |
| <Sx*> |  |  | 71.2 |  |  | 74.8 |

*SPIKE WITH 26.3 ul PANEL 5 = 1.23 PEIU/ml (PANEL 7)

What is claimed is:

1. An immunoassay for detection of anti-hepatitis B core (HBc) antibodies in a biological sample which immunoassay utilizes recombinantly derived Hbc antigen comprising the steps of:
   (a) reacting a solid phase coated with the HBc antigen with the biological sample for a time and under conditions sufficient to form antigen/antibody complexes;
   (b) reacting said complexes with a labeled anti-Hbc antigen antibody;
   (c) detecting the amount of labeled anti-Hbc antigen antibody bound to the solid base;
   wherein the improvement comprises adding a reducing agent to the biological sample prior to performing step (a) or step (b).

2. The immunoassay of claim 1 wherein said reducing agent is a sulfydral compound.

3. The immunoassay of claim 2 wherein the sulfydral reducing compound is selected from the group consisting of 2-mercaptoethanol, dithiothreitol, dithioerythritol, cysteine and bisulfite solutions.

4. An immunoassay for detection of antibodies to hepatitis B core (Hbc) antigen in a biological sample comprising:
   (a) contacting a biological sample with microparticles coated with recombinantly derived Hbc antigen and a reducing agent to form a reaction mixture;
   (b) transferring said reaction mixture to a microparticle capture/flow through filter;
   (c) adding a labeled anti-Hbc antigen antibody to the capture filter and incubating same for a time and under conditions sufficient to form reaction mixture/labeled antibody complexes;
   (d) detecting the label to determine the amount of antibody to the Hbc antigen in the biological sample.

5. The immunoasay of claim 4 wherein the reducing agent is a sulfydral compound.

6. The immunoassay of claim 5 wherein the sulfydral reducing compound is selected from the group consisting of 2-mercaptoethanol, dithiothreitol, dithioerythritol, cysteine and bisulfite solutions.

7. The immunoassay of claim 4 wherein said label is acridinium.

8. The immunoassay of claim 4 wherein said Hbc antigen is recombinantly produced.

9. In an immunoassay for detection of anti-hepatitis B core (HBc) antibodies in a biological sample comprising the steps of:
   (a) reacting a solid phase coated with recombinantly produced HBc antigen with the biological sample for a time and under conditions sufficient to form antigen/antibody complexes;
   (b) reacting said complexes with a labeled anti-Hbc antigen antibody;
   (c) detecting the amount of labeled anti-Hbc antigen antibody bound to the solid phase;
   wherein the improvement comprises adding a reducing agent to the biological sample prior to performing step (a) or step (b).

* * * * *

UNITED STATES PATENT AND TRADEMARK OFFICE
CERTIFICATE OF CORRECTION

PATENT NO. : 6,150,113
DATED : November 21, 2000
INVENTOR(S) : Richard H. Decker et al.

It is certified that error appears in the above-identified patent and that said Letters Patent is hereby corrected as shown below:

<u>Column 11,</u>
Line 51, replace "bound to the solid base;" with -- bound to the solid phase; --.

Signed and Sealed this

First Day of January, 2002

Attest:

*Attesting Officer*

JAMES E. ROGAN
*Director of the United States Patent and Trademark Office*